United States Patent
Tsung et al.

(10) Patent No.: US 7,262,409 B2
(45) Date of Patent: Aug. 28, 2007

(54) CHEMICAL ETCH SOLUTION AND TECHNIQUE FOR IMAGING A DEVICE'S SHALLOW JUNCTION PROFILE

(75) Inventors: Lancy Y. Tsung, Plano, TX (US); Adolfo Anciso, Garland, TX (US); Doug Matheson, Allen, TX (US)

(73) Assignee: Texas Instruments Incorporated, Dallas, TX (US)

( * ) Notice: Subject to any disclaimer, the term of this patent is extended or adjusted under 35 U.S.C. 154(b) by 73 days.

(21) Appl. No.: 11/028,833

(22) Filed: Jan. 4, 2005

(65) Prior Publication Data
US 2006/0145073 A1    Jul. 6, 2006

(51) Int. Cl.
*H01L 21/00*    (2006.01)
(52) U.S. Cl. ............... 250/307; 252/79.1; 252/79.2; 252/79.4; 156/345.29
(58) Field of Classification Search ........... 438/705, 438/745
See application file for complete search history.

(56) References Cited

U.S. PATENT DOCUMENTS 6,666,986 B1 *    12/2003    Vaartstra .......... 252/79.1

OTHER PUBLICATIONS

Sheng, T. T., et al., "Delineation of Shallow Junctions in Silicon by Transmission Electron Microscopy," *Journal of the Electrochemical Society*, vol. 128, No. 4, Apr. 1981, pp. 881-884.
Cerva, Hans, "Two-dimensional delineation of shallow junctions in silicon by selective etching of transmission electron microscopy cross sections," *J. Vac. Sci. Technol. B*, vol. 10, No. 1, Jan./Feb. 1992, 3 pages.

* cited by examiner

*Primary Examiner*—David A. Vanore
(74) *Attorney, Agent, or Firm*—Peter K. McLarty; W. James Brady, III; Frederick J. Telecky, Jr.

(57) ABSTRACT

The present invention provides, in one aspect, a method of imaging a microelectronics device 100. The method comprises cleaning, when contaminants are preset, a sample of a microelectronics device 100 to be imaged with a first solution comprising hydrofluoric acid, an inorganic acid and water, exposing the sample to a second solution comprising hydrofluoric acid, an inorganic acid and an organic acid, wherein the second solution forms a contrast between different regions within the sample, and producing an image of the contrasted sample.

10 Claims, 3 Drawing Sheets

CHEMICAL ETCH SOLUTION AND TECHNIQUE FOR IMAGING A DEVICE'S SHALLOW JUNCTION PROFILE

TECHNICAL FIELD OF THE INVENTION

The present invention is directed in general to the manufacture of semiconductor devices, and, more specifically, to a chemical etch solution and technique for imaging device's shallow junction profile.

BACKGROUND OF THE INVENTION

The continuing push to produce faster microelectronic devices with lower power consumption has resulted in the miniaturization of such devices. In particular, smaller gate length and channel lengths are conducive to the low voltage and faster operation of transistor devices, such as complementary metal oxide semiconductor (CMOS) transistors. However, with shrinking process geometries, a number of new design problems arise.

For instance, as gate dimensions are reduced, it has become necessary to adjust and better control the dimensions of the channel and doped regions of the substrate that are associated with the gate. This is necessary to prevent a number of short channel effects such as, threshold voltage variation, drain induced barrier lowering (DIBL), punch-through, leakage currents, hot carrier injection, and mobility degradation.

Consider, for instance, the dimensions of shallow junctions and pocket region structures. Shallow junctions, also referred to as source drain extensions, or light or medium-doped drain (LDD and MDD, respectively) regions, are implanted as extensions to the larger and more heavily doped source and drain regions, to reduce hot carrier injection-induced damage to gate dielectric layers and improve short channel effects. Hot carriers, electrons with higher than average energy, form because of the stronger electric fields produced in small transistor device geometries. Shallow junctions, implanted before sidewall formation and source and drain implantation, provide a doping gradient between the source and drain regions and the channel. The lowered electric field in the vicinity of the channel region of such devices reduces the formation of hot carriers.

Sub-0.1 micron transistor devices are also highly susceptible to leakage currents, or punch-through, when the transistor is off. These conditions can arise when the shallow junctions and the source/drains are not properly formed. Thus, leakage currents can be reduced if the shallow junctions are formed with well-defined boundaries, as exemplified by an abrupt decrease in dopant concentration, to support low-voltage operation of the transistor and to define the width of the channel region of the transistor.

Unfortunately, however, it can be very difficult to ascertain any irregularities in these shallow junctions or source/drain areas using standard imaging techniques. This is largely attributable to the fact that these shallow junctions do not show up in the cross section scans of an imaging tool, such as a scanning electron microscope (SEM) or a transmission electron microscope (TEM). Thus, it can be very difficult to ascertain with any degree of certainty what structural defects or irregularities might exist in the junction or gate areas of the microelectronics device.

Accordingly, what is needed in the art is an improved method of obtaining an image of the junctions areas of a microelectronics device.

SUMMARY OF THE INVENTION

To address the above-discussed deficiencies of the prior art, the present invention provides a method of imaging a shallow junction profile in a microelectronics device. In one embodiment, the method comprises cleaning a sample of a microelectronics device to be imaged with a first solution comprising hydrofluoric acid, an inorganic acid and water, exposing the sample to a second solution comprising hydrofluoric acid, an inorganic acid and an organic acid, wherein the second solution forms a contrast between different regions within the sample, and producing an image of the sample.

In another embodiment, there is provided a method of manufacturing an integrated circuit. This particular embodiment comprises forming at least a portion of an integrated circuit on a microelectronic device substrate using a fabrication process and preparing a test sample from the portion of the integrated circuit. The test sample is exposed to a contrast solution comprising hydrofluoric acid, an inorganic acid and an organic acid, wherein the contrasting solution forms a contrast between different regions within the test sample. An image of the contrasted test sample is produced to determine if the test sample falls within a specified parameter. If the test sample falls outside the specified parameter, the fabrication process is adjusted to bring an integrated circuit produced by the fabrication process within the specified parameter. The adjusted fabrication process is then used to fabricate an operative integrated circuit.

The foregoing has outlined preferred and alternative features of the present invention so that those of ordinary skill in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the scope of the invention.

BRIEF DESCRIPTION OF THE DRAWINGS

The invention is best understood from the following detailed description when read with the accompanying FIGURES. It is emphasized that in accordance with the standard practice in the semiconductor industry, various features may not be drawn to scale. In fact, the dimensions of the various features may be arbitrarily increased or reduced for clarity of discussion. Reference is now made to the following descriptions taken in conjunction with the accompanying drawings, in which.

DETAILED DESCRIPTION

Figure 1:
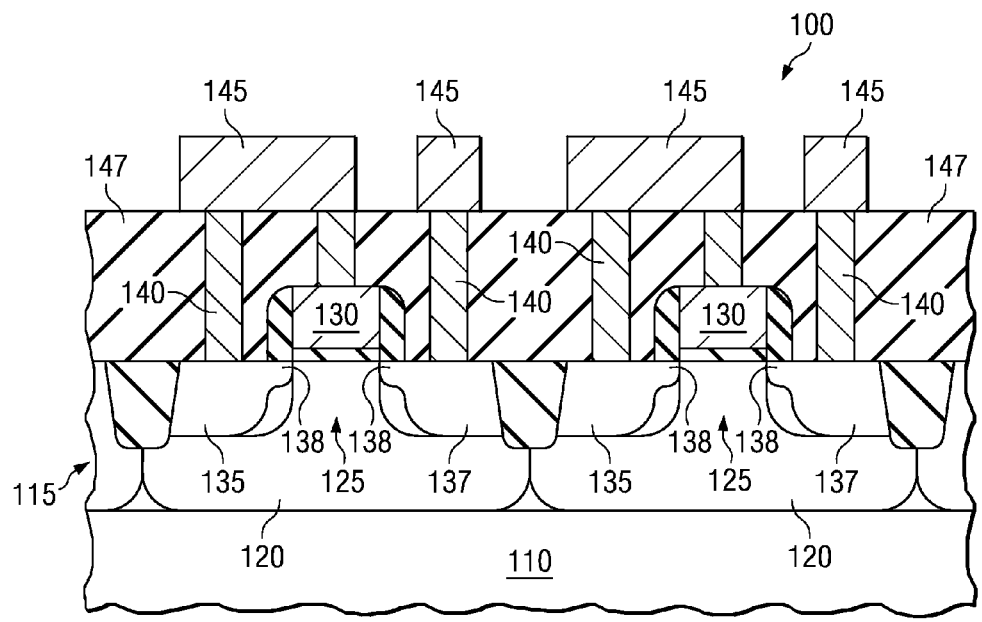
FIG. 1 illustrates a partial sectional view of microelectronics device at an early stage of manufacture and with which the present invention can be implemented

Turing initially to FIG. 1, there is illustrated a partial, sectional view of an exemplary integrated circuit 100 at the first metal level that is located over a device level. At this point of manufacture, the integrated circuit 100 is of conventional design and includes a substrate 110, such as a microelectronics substrate on which sub-micron devices can be built. The substrate 110 may be configured to serve as a well region for the integrated circuit 100, or it might have an epitaxial layer 115 located thereover in which wells 120 are formed. The wells 120 may be complementary wells, such as an N-type well and a P-type well, respectively, however, other well known doping configurations are also applicable. The integrated circuit 100 further comprises conventional transistors 125, such as complementary NMOS and PMOS transistors, that may include gates 130 and source/drain regions 135, 137, respectively. These source/drain regions 135, 137 are often referred to as junctions and can often include lightly doped and halo extensions 138. The spacing between these junctions under the gate define the channel length, and this spacing, as well as their doping profiles, can have critical implications on the operation of the microelectronics device 100. As such, it is highly beneficial that these junctions be as close to design specifications as possible. Also shown in FIG. 1 are contacts 140, which connect the gates 130 and source/drains 135, 137 of each of the transistors 125 to overlying metal interconnect structures 145 formed on an interlevel dielectric layer 147.

The present invention provides a unique method for imaging the doped junction areas of the microelectronic device 100. In an advantageous embodiment, the sample may be sectioned by using a focused ion beam. It has been found that in some cases, the focused ion beam process can contaminate the sample with gallium. With the present invention, it has presently been found that contaminants, including gallium, can interfere with or inhibit obtaining a good contrast image of the microelectronics device 100, particularly in the junction region of the device. Thus, in one embodiment, the present invention recognizes the need to remove such contaminants from the sample to obtain a high quality image of the cross section of the microelectronics device 100 for more accurate analysis. It should be understood, however, that in those instances where the sample can be sectioned by methods that significantly reduce such contaminants, the removal step may not be necessary.

In those embodiments where contaminants are present, one embodiment comprises cleaning the sample of the microelectronics device 100 with a first solution, such as a cleaning solution. The first solution comprises a mixture of hydrofluoric acid, an inorganic acid, and water. It should be noted that the sample may be taken from a product line, or it may be a test sample made with the same process used to make the actual product.

The inorganic acid of the first solution is preferably a strong inorganic acid having a $pK_a$ of about −1.0 or less. In one embodiment, the inorganic acid is nitric acid. However, in other embodiments, the inorganic acid may be hydrochloric acid, hydrobromic acid, hydroiodic acid, perchloric acid, or sulfuric acid. While, the concentrations of the various components of the first solution may vary, it has been found that an advantageous solution comprises from about 1 to about 3 parts by volume of 5% hydrofluoric acid, from about 2 parts to about 4 parts by volume of 70% strong inorganic acid, and from about 4 parts to about 6 parts by volume of water, preferably dionized water. More preferably, the first solution comprises about 2 parts 5% hydrofluoric acid, about 3 parts 70% nitric acid and about 5 parts dionizied water. It has been found that using the first solution removes contaminants, such as gallium, that are present from the sample, which provides a better contrast in the image.

The period of time during which the sample microelectronics device 100 is exposed to the first solution may also vary. For example, in one embodiment, the sample may be placed in the first solution for a period of time ranging from about 15 seconds to about 20 seconds and at a temperature ranging from about 22 to about 30 degrees centigrade. In a more advantageous embodiment, however, the sample is placed in the first solution for about 15 seconds at a temperature of about 22 degrees centigrade.

A contrast solution is used to provide a contrast in the sample of the microelectronic device 100. The sample, as described below, is placed in the contrast solution for a period of time. The contrast solution may be used by itself in those instances where the cleaning step is not necessary to obtain a good image. Alternatively, the contrast solution may be used in sequence with the above-discussed first or cleaning solution. In such instances, the contrast solution is a second solution in the process. In an exemplary embodiment, the contrast or second solution to which the sample is exposed comprises a mixture of hydrofluoric acid, an inorganic acid, and an organic acid.

The inorganic acid of the contrast or second solution is preferably a strong inorganic acid having a $pK_a$ of about −1.0 or less, and the organic acid is a weak acid having a $pK_a$ of about 2.76 or greater. In one embodiment, the inorganic acid is nitric acid. However, in other embodiments, the inorganic acid may be hydrochloric acid, hydrobromic acid, hydroiodic acid, perchloric acid, or sulfuric acid. The organic acid, on the other hand, may be, in one embodiment, acetic acid. In another embodiment, however, the organic acid may be butonoic acid, formic acid, or propinoic acid. Other organic acids that contain carbon and have the appropriate $pK_a$ value are also within the scope of the present invention. While, the concentrations of the various components of the contrast or second solution may vary, it has been found that an advantageous solution comprises from about 1 to about 3 parts by volume of 5% hydrofluoric acid, from about 2 parts to about 4 parts by volume of 70% strong inorganic acid, and from about 4 parts to about 6 parts of 99% organic acid. More preferably, the contrast solution comprises about 2 parts 5% hydrofluoric acid, about 3 parts 70% nitric acid and about 5 parts 99% acetic acid. It has been found that using the second solution provides a much improved image over those previously used and thereby allows for more accurate analysis of the sample, as is shown in the following figures.

The period of time during which the sample microelectronics device 100 is exposed to the contrast or second solution may also vary. For example, in one embodiment, the sample may be placed in the contrast solution for a period of time ranging from about 3 seconds to about 16 seconds and at a temperature ranging from about 22 to about 30 degrees centigrade. In a more advantageous embodiment, however, the sample is placed in the contrast or second solution for about 8 second at a temperature of about 22 degrees centigrade.

Following the exposure to the contrast solution, an image of the sample of the microelectronic device 100 can be taken with an image device, such as a transmission electron microscope (TEM), a scanning electron microscope (SEM) or a focused ion beam (FIB) microscope.

Figure 2:
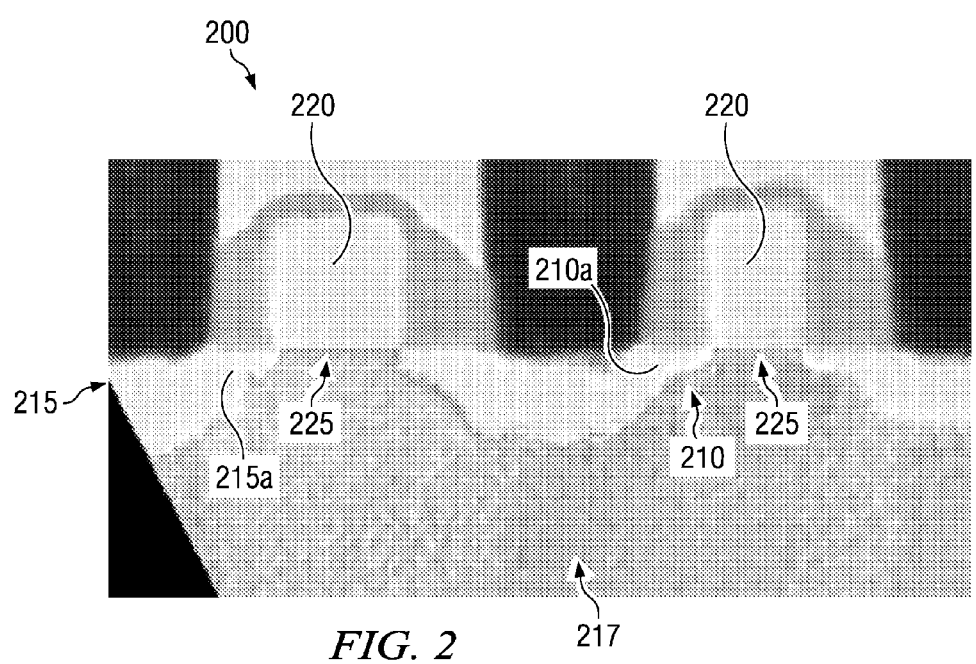
FIG. 2 illustrates an image of junction regions of a microelectronics device taken with a transmission electron microscope after being prepared in accordance with the principles of the present invention.

Referring now to FIG. 2, there is illustrated an image of a microelectronics device 200 having junction regions 210, 215, which in this case are source/drain regions for gates 220, taken with a TEM, after being prepared in accordance with the principles of the present invention. In this particular embodiment, the microelectronics device 200 was cleaned with the first solution, as discussed above. As seen in this figure, substantial detail of the junction regions' 210, 215 dopant profiles are clearly contrasted with the well 217 in which junction regions 210 and 215 are located and are very visible, including their respective lightly doped areas 210a and 215a, which define the channel length region 225 of the microelectronics device 200.

Given the amount of detail that is present in this image, a variant or malformed junction dopant profile or invariant channel length could easily be determined. This information could then be used to provide a possible explanation for any deficient operation or qualitative test failure of the microelectronics device 200. Moreover, the information obtained from the image could then be used to adjust the out-of-specification fabrication process, such as a dopant implant parameter, to correct the manufacturing problem.

The contrast or second solution, as discussed above, reacts with the dopant and the silicon in the sample to provide the contrast between the junctions 210 and 215 and the well 217. In essence, the silicon in the doped junction regions 210 and 215 is substantially or completely removed, which provides the contrast between the denser material that is not significantly affected by the contrast solution and the less dense material that is so affected. Also, as seen in FIG. 2, the junctions 210 and 215 are not the only part of the microelectronics device 200 that is affected by the solution. In addition, the gate 220 can also be affected by the solution when doped appropriately. In an advantageous embodiment, the junctions 210 and 215 and the gates 220 are doped with an N-type dopant, such as arsenic. Additionally, while the dopant concentration may vary, depending on the design of the microelectronics device 200, the dopant concentration within the junctions 210 and 215 can range from about 5E13 atoms/cm$^3$ to about 5E15 atoms/cm$^3$ in an advantageous embodiment. It is believed that the dopant concentration does have an effect on the quality of the image. For example, if the dopant concentration is too light, then the contrast solution may not provide a good contrast of the image.

Figure 3:
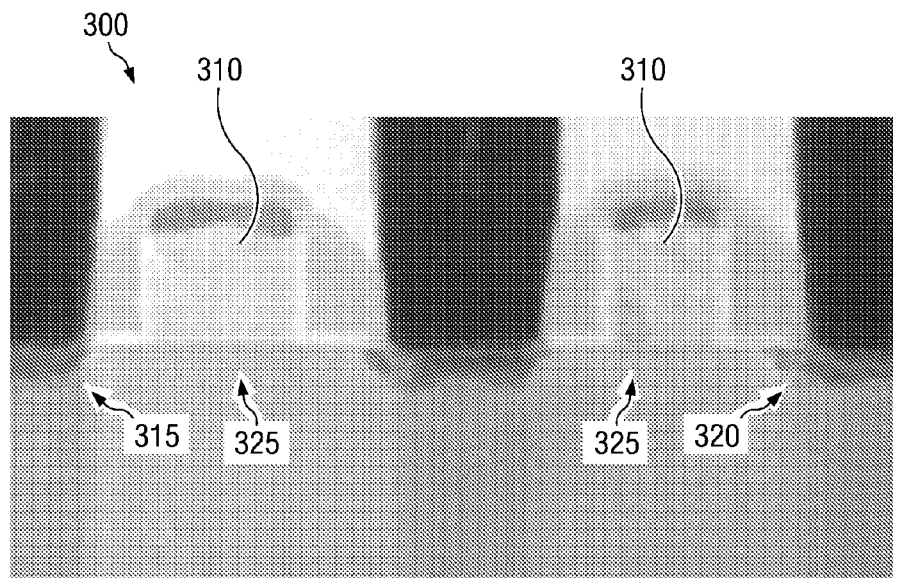
FIG. 3 illustrates an image of a sample of a microelectronics device wherein the present invention has not been utilized, thereby showing a lack of contrast between the junction regions and the well.

In stark contrast to FIG. 2, FIG. 3 is a TEM image of a microelectronic devices 300, which include gates 310 and source/drain junctions 315 and 320, that was prepared by conventional methods and, therefore, without the benefits provided by the present invention. As seen from this image, there is no contrast between the junction regions 315 and 320 and the wells 325 in which junctions 315 and 320 are formed. As such, this image could not be used to determine the possible source of any defect within the junction profile or gate regions of the microelectronics devices 300. Consequently, it would be extremely difficult, if not impossible, to determine if any particular fabrication process was the source of the defect.

Figure 4:
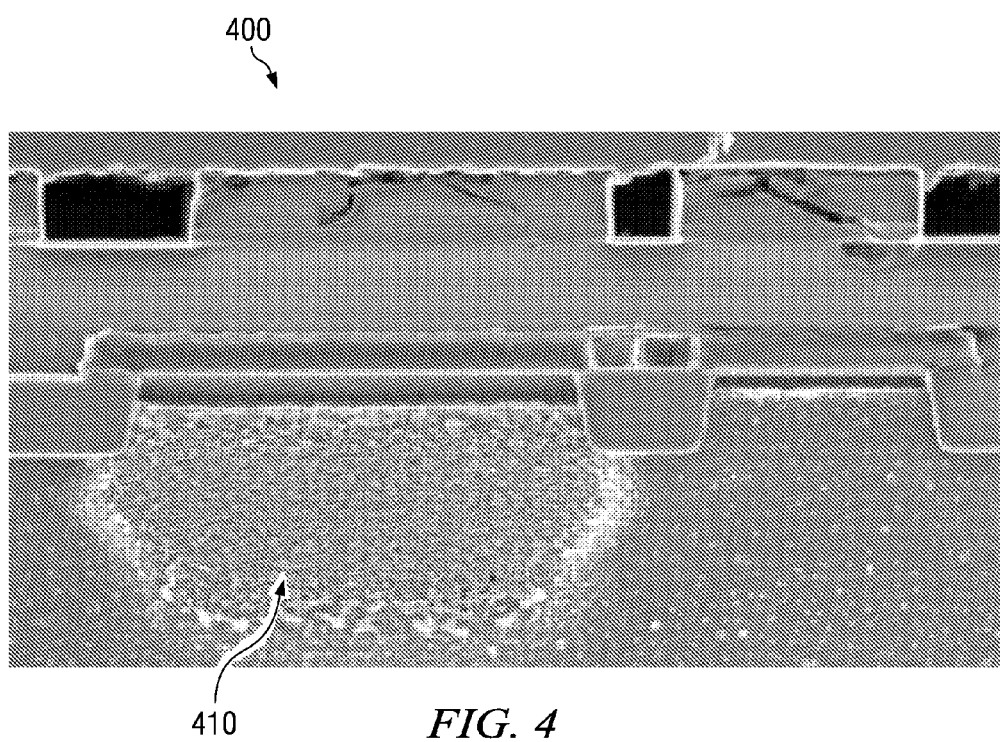
FIG. 4 illustrates an image of a well region of a microelectronics device taken with a scanning electron microscope after being prepared in accordance with the principles of the present invention.

FIG. 4 illustrates a TEM image of microelectronics device 400 having a well region 410. As seen in this figure, the present invention can also be used to contrast the well region 410 so that its dopant profile can be ascertained. In this particular embodiment, the contrast or second solution has caused topographical relief within the well region 410. The topographical relief provides the contrast and outlines the profile of the well 410. Thus, this can be use in conjunction with the foregoing embodiments to image aspects of a microelectronics device that have not previously been easily imaged, and through these images structural irregularities can be determined and particular fabrication processes can be targeted for adjustment.

Figure 5:
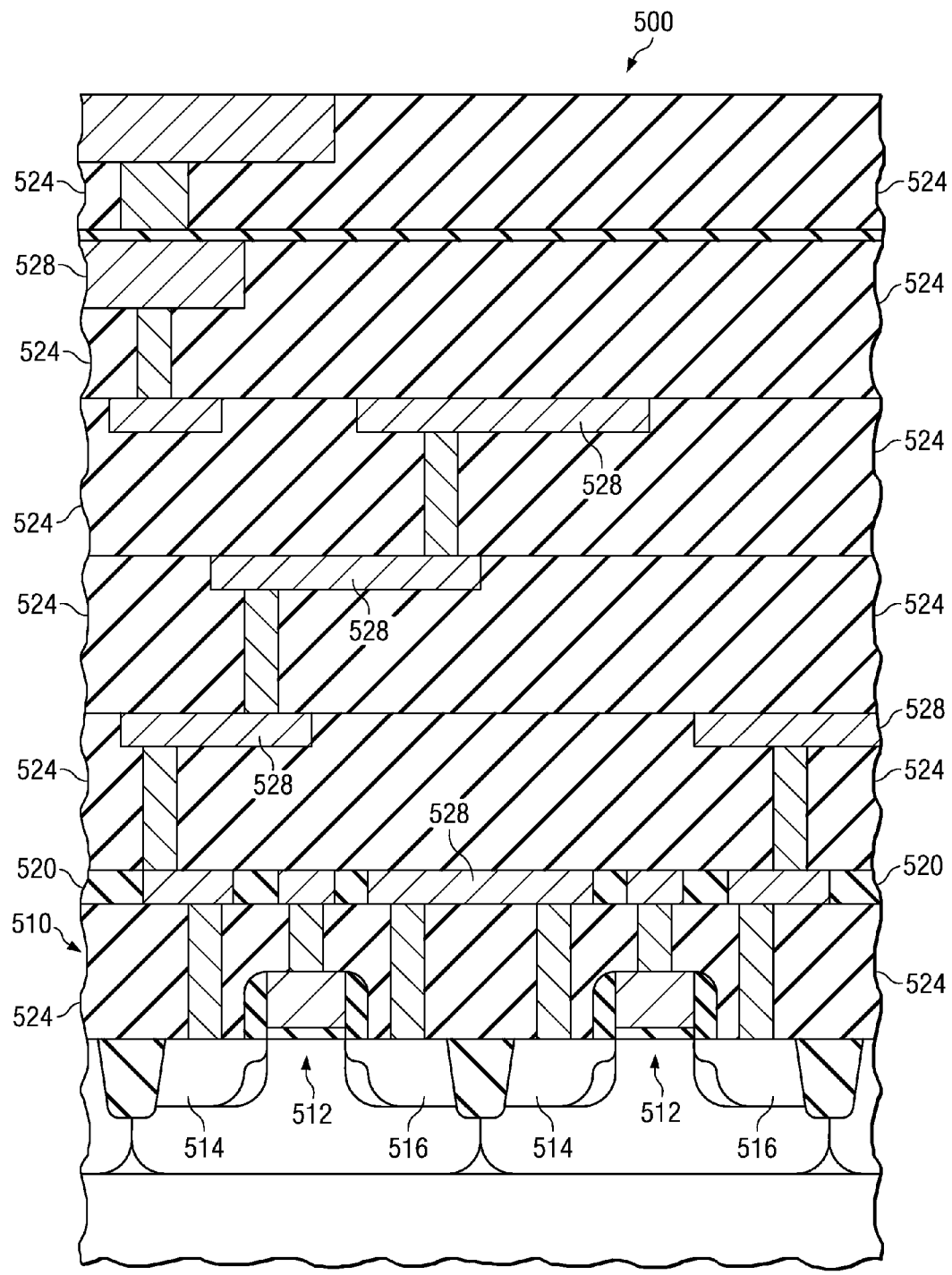
FIG. 5 is a partial sectional view of an integrated circuit that can be constructed using the present invention.

FIG. 5 illustrates a partial view of an integrated circuit 500. FIG. 5, briefly illustrates a partial view of an integrated circuit 500. The integrated circuit includes transistors 512 of conventional design having source/drain junctions 514 and 516, as discussed above. Located over the transistors 512 are conventionally formed dielectric layers 524 having conventionally formed interconnects 528, such as vias, metal lines and contact plugs located therein. The interconnects 528 electrically connect the transistors 512 to form an operative integrated circuit.

The present invention could be used to fabricate the integrated circuit 500 in the following way. When a product is produced a test sample of that product could be taken and sectioned with a focused ion beam. The test sample could then be cleaned, if required, in the manner described above. The test sample would then be placed in the contrast or second solution to cause contrast regions to form, which would be detectable with a TEM. If there was an irregularity, for example, in the dopant profile of the junction region, the doping implantation process could be targeted for adjustment to bring the dopant profile within specification. For instance, the dopant profile may be too deep, or it may extend to far under the gate, thereby causing the channel to be too narrow, either of which could affect transistor performance. When given this information, one skilled in the art could then adjust the implant parameters to correct the structural defects. The adjusted process could then be used to fabricate another batch of devices or test samples, which would then be examined using the present invention. If the structural defects were corrected, then no further adjustments would have to be made to the fabrication process. However, if detectable portions of the microelectronics device continued to be out of specification, then further adjustments could be made to the fabrication process.

Although the present invention has been described in detail, one of ordinary skill in the art should understand that they can make various changes, substitutions and alterations herein without departing from the scope of the invention.

What is claimed is:

1. A method of manufacturing an integrated circuit, comprising:

forming at least a portion of an integrated circuit on a microelectronic device substrate using a fabrication process;

preparing a test sample from at least the portion of the integrated circuit, comprising:

exposing the test sample to a contrast solution comprising hydrofluoric acid, an inorganic acid and an organic acid, the solution forming a contrast between different regions within the test sample, wherein the inorganic acid is a strong inorganic acid having a $pK_a$ of about −1.0 or less and the organic acid is a weak acid having a $pK_a$ of about 4.5 or greater, wherein the inorganic acid is hydrochloric acid, hydrobromic acid, hydroiodic acid, perchloric acid, or sulfuric acid and wherein the organic acid of the contrast solution is butonoic acid, formic acid, or propinoic acid; and producing an image of the test sample to determine if the test sample falls within a specified parameter;

adjusting the fabrication process to bring an integrated circuit produced by the fabrication process within the specified parameter if the test sample is outside of the specified parameter; and using the adjusted fabrication process to fabricate an operative integrated circuit.

2. The method as recited in claim 1, wherein forming at least the portion includes forming a junction in the microelectronics device substrate wherein the junction is doped with an N-type dopant.

3. The method as recited in claim 2, wherein adjusting includes adjusting a dopant implant parameter to change a dopant profile of the junction.

4. The method as recited in claim 1 wherein preparing further includes cleaning the sample with a cleaning solution, wherein the cleaning solution comprises hydrofluoric acid, the inorganic acid, and water.

5. The method as recited in claim 4 wherein the inorganic acid is nitric acid and the organic acid is acetic acid.

6. The method as recited in claim 5, wherein the cleaning solution is a solution of from about 1 to about 3 parts by volume of 5% hydrofluoric acid, from about 2 parts to about 4 parts by volume of 70% nitric acid, and from about 4 parts to about 6 parts by volume of water.

7. The method as recited in claim 1 wherein the contrast solution is a solution of from about 1 part to about 3 parts by volume of 5% hydrofluoric acid, from about 2 parts to about 4 parts by volume of 70% nitric acid, and from about 4 parts to about 6 parts by volume 99% acetic acid.

8. The method as recited in claim 6, wherein cleaning includes placing the sample into the cleaning solution for a period of time ranging from about 15 seconds to about 20 seconds and at a temperature ranging from about 22 to about 30 degrees centigrade and wherein exposing includes placing the sample into the contrast solution for a period of time ranging from about 3 seconds to about 16 seconds and at a temperature ranging from about 22 to about 30 degrees centigrade.

9. The method as recited in claim 1, wherein producing an image includes producing an image of the sample with a transmission electron microscope, a scanning electron microscope or a focused ion beam microscope.

10. The method as recited in claim 9, wherein preparing a test sample includes preparing the test sample with a focused ion beam and producing an image includes producing the image with a transmission electron microscope.

* * * * *